(12) United States Patent
Doyle et al.

(10) Patent No.: US 6,399,393 B1
(45) Date of Patent: Jun. 4, 2002

(54) CRYOGENIC HOMOGENIZATION AND SAMPLING OF HETEROGENEOUS MULTI-PHASE FEEDSTOCK

(75) Inventors: Glenn Michael Doyle, Lakewood; Virgene Linda Ideker, Arvada; James David Siegwarth, Boulder, all of CO (US)

(73) Assignee: The United States of America as represented by the Department of Energy, Washington, DC (US)

( * ) Notice: Subject to any disclaimer, the term of this patent is extended or adjusted under 35 U.S.C. 154(b) by 0 days.

(21) Appl. No.: 09/400,822

(22) Filed: Sep. 21, 1999

(51) Int. Cl.[7] .............................. G01N 1/04; B09B 3/00
(52) U.S. Cl. ...................... 436/174; 588/200; 588/205; 588/251; 588/252; 588/900; 62/320; 62/321
(58) Field of Search ........................... 436/174; 588/900, 588/200, 205, 251, 252; 62/320, 321

(56) References Cited

U.S. PATENT DOCUMENTS

| | | |
|---|---|---|
| 4,846,408 A | 7/1989 | Sallavanti et al. |
| 5,520,004 A | 5/1996 | Jones, III |
| 5,735,471 A | 4/1998 | Muro |
| 5,769,335 A | 6/1998 | Shutov |
| 5,792,219 A | 8/1998 | Hartman et al. |

FOREIGN PATENT DOCUMENTS

EP 0702076 * 3/1996

* cited by examiner

*Primary Examiner*—T. Tung
*Assistant Examiner*—Monique T. Cole
(74) *Attorney, Agent, or Firm*—Mark F. LaMarre; Thomas G. Anderson; Virginia B. Caress

(57) ABSTRACT

An apparatus and process for producing a homogeneous analytical sample from a heterogenous feedstock by: providing the mixed feedstock, reducing the temperature of the feedstock to a temperature below a critical temperature, reducing the size of the feedstock components, blending the reduced size feedstock to form a homogeneous mixture; and obtaining a representative sample of the homogeneous mixture. The size reduction and blending steps are performed at temperatures below the critical temperature in order to retain organic compounds in the form of solvents, oils, or liquids that may be adsorbed onto or absorbed into the solid components of the mixture, while also improving the efficiency of the size reduction. Preferably, the critical temperature is less than 77 K (−196° C.). Further, with the process of this invention the representative sample may be maintained below the critical temperature until being analyzed.

14 Claims, 11 Drawing Sheets

CRYOGENIC HOMOGENIZATION AND SAMPLING OF HETEROGENEOUS MULTI-PHASE FEEDSTOCK

The United States Government has rights in this invention pursuant to the employer-employee relationship of the U.S. Department of Energy and the inventor.

BACKGROUND OF THE INVENTION

1. Field of the Invention

This invention relates to a method and apparatus for homogenizing and sampling heterogeneous feedstock. More particularly, this invention relates to a method for providing a representative sample from heterogeneous feedstock containing solids, liquids, and volatile compounds that vaporize under standard atmospheric conditions.

2. Description of Related Art

Hazardous and/or radioactive materials are typically present in two forms, primary sources of contamination and secondary hazardous waste. Examples of primary sources of contamination are radioactive, chemical or biological materials. Primary sources of contamination by their nature present an increased risk to human health and the environment upon exposure and must be maintained and stored in such a manner as to prevent contact with both.

The handling of primary sources of contamination results in the generation of secondary wastes. Typically, secondary waste is a heterogeneous mixture of materials, such as protective clothing, polyethylene air canisters, handling equipment, sample bags, and laboratory sampling accessories (e.g., laboratory wipes, glassware, and swabs). Protective clothing may be in the form of full body suits, goggles, face masks, boots, and gloves. This secondary heterogeneous waste may be made from materials such as paper, cloth, vinyl, rubberized material, Tyvek®, or metal. This secondary heterogeneous waste may be contaminated with organic compounds in the form of solvents, oils, liquids or in combination with each other and/or inorganic compounds or elements. The proper storage, treatment and disposal of the secondary heterogeneous waste depend on the type of contamination.

Typically, secondary heterogeneous waste is retained after use in appropriate containment vessels until a sufficient quantity of material is collected for disposal. Under parts 261 and 268 of the Resource Conservation and Recovery Act (RCRA), prior to final treatment or disposal, the secondary heterogeneous waste must be characterized to determine the proper treatment and disposal regime. The current procedure for obtaining samples involves personnel dressed in appropriate personal protective equipment opening the containers, reaching into the secondary heterogeneous waste matrix with a knife or scissors, cutting randomly-selected pieces of soft waste materials at different levels within the container, depositing them into sample jars, labeling them and sending them for appropriate analysis in accordance with Environmental Protection Agency (EPA) Publication SW-846. Due to the variability of the material that is contained in each vessel it may be difficult to generate a statistically representative sample of a small enough size, for later chemical and physical analysis. Normally, with this sampling method, items within each vessel may be missed, thereby providing inaccurate information for storage, treatment or disposal compliance purposes. Further, this method also exposes the sample taker unnecessarily to radiation and/or chemical hazards.

Another problem associated with sampling the secondary heterogeneous waste is how to accurately capture volatile organic compounds at the detection limits required under the regulations. Oftentimes, hazardous chemical constituents adsorbed onto, or absorbed into the soft waste matrices are not properly detected in the samples. This may be due to matrix effects, sampling error, the inherent inaccuracy of the current sampling method, or a combination of any or all of these.

BRIEF SUMMARY OF THE INVENTION

An object of this invention is to provide a representative sample from heterogenous feedstock.

Another object of this invention is to provide a process that will retain volatile organic compounds contained within a feedstock during the sampling procedure.

Another object of this invention is to provide a process that is consistent with the hazardous waste regulations.

Another object of this invention is to provide a process that reduces the number of samples required to adequately characterize a population of heterogeneous waste.

Another object of this invention is to provide a contained apparatus such that the apparatus is maintained at cryogenic operating conditions and minimize the spread of radioactive and/or hazardous material and personnel exposure.

These and other objectives of the invention, which will become apparent from the following description, have been achieved by a novel apparatus and process for providing a homogeneous analytical sample comprising: providing a heterogenous feedstock having an average initial particle size; reducing the temperature of the heterogeneous feedstock to a temperature below a critical temperature; conveying the heterogeneous feedstock (rubber, latex, plastic, paper or wood) to a size reduction device; reducing the size of the feedstock components; blending the reduced size feedstock to form a homogeneous mixture; obtaining a representative sample of the homogeneous mixture. Critical temperature is used herein to mean a temperature below which a significant portion of the feedstock is embrittled such that it will break or fracture upon bending, as opposed to flexing, as well as retain the volatile organic compounds. Preferably, the critical temperature is less than about 100 K (−173° C.). Herein, heterogeneous feedstock refers to a mixture of materials having a wide variability in size (e.g., supplied air suits which are 6 feet×2 ft to paper tissue which is 1 in×2 inches) and chemical compositions. The heterogeneous feedstock further comprises rigid solids, flexible solids, liquids, and volatile organic compounds. The volatile organic compounds may include, but are not limited to, methyl ethyl ketone (MEK), carbon tetrachloride, benzene, toluene and vinyl chloride. Preferably, the process of this invention maintains the representative sample below the critical temperature prior to being analyzed. Preferably, the size reduction and blending step are maintained at or below the critical temperature. Preferably, the process of this invention maintains the representative sample below 100 K (−173° C.) and more preferably 77 K (−196° C.) prior to being analyzed. The process is such that volatile organic compounds present in the feedstock are retained in the representative sample. Preferably liquid nitrogen is used to reduce the temperature of the feedstock below the critical temperature and maintain the temperature below the critical temperature.

BRIEF DESCRIPTION OF THE SEVERAL VIEWS OF DRAWINGS

With this description of the invention, a detailed description follows with reference being made to the accompanying figures of drawings which form part of the specification, in which like parts are designated by the same reference numbers, and of which:

The invention is not limited in its application to the details and construction and arrangement of parts illustrated in the accompanying drawings since the invention is capable of other embodiments that are being practiced or carried out in various ways. Also, the phraseology and terminology employed herein are for the purpose of description and not of limitation.

DETAILED DESCRIPTION OF THE INVENTION

Description of the Preferred Embodiment(s)

Figure 1:
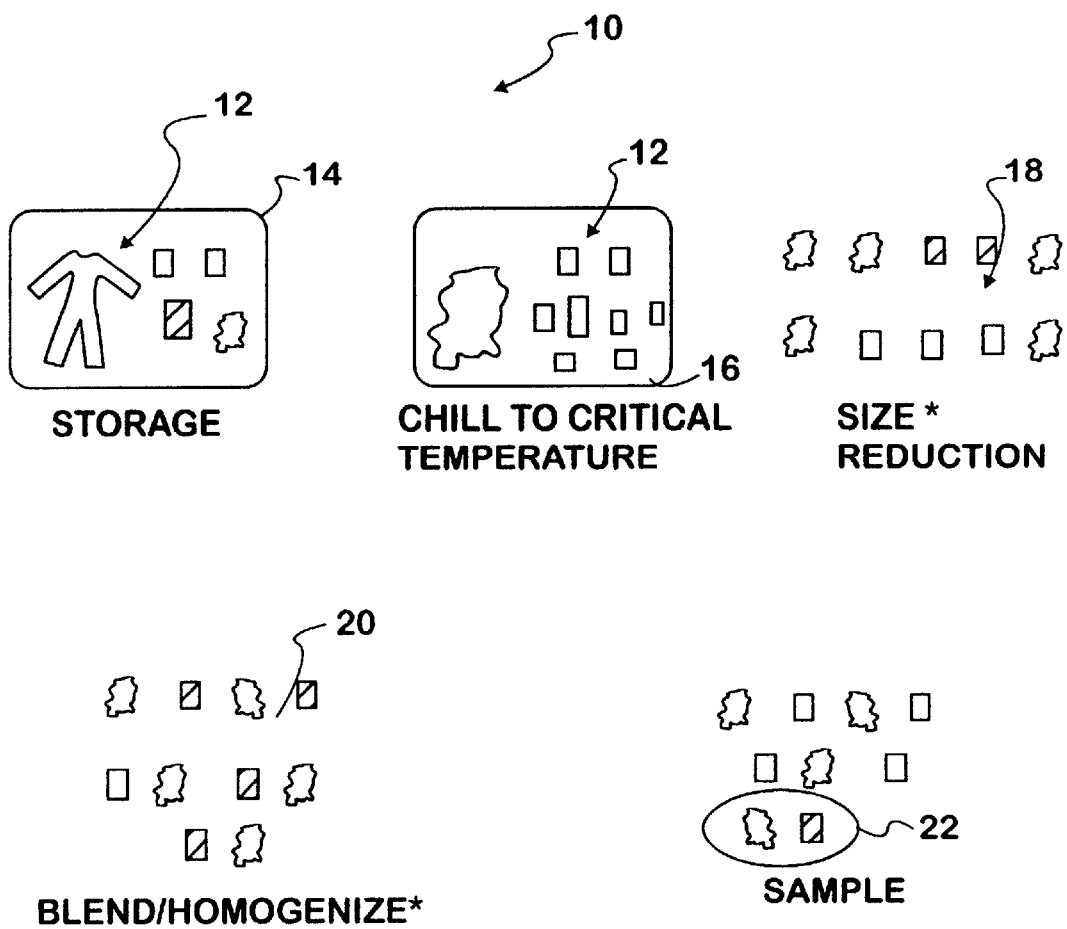
FIG. 1 is a schematic view of the process of this invention.

The process of this invention is shown generally at 10 in schematic form in FIG. 1. Typically, the feedstock of heterogeneous material 12 is stored in vessels 14, e.g., 55 gallon steel drums. The feedstock may contain protective bodysuits, boots, goggles, rags, laboratory tissues (commonly known as KIMWIPES®) and various protective clothing and accessories. The heterogeneous feedstock contains a mixture of materials, such as, but not limited to paper, vinyl, rubber, plastic, and wood, which may be contaminated with a wide range of inorganic and organic compounds and/or radioactive components. The compounds from which the feedstock is made include a wide range of chemical compounds (straight chain polymers, branched chain polymers, cyclic organic, cellulosic, and aromatics). The feedstock has a wide variability in size (e.g., supplied air suits which are 6 feet×2 ft to paper tissue which is 1 in×2 inches). The heterogeneous material 12 is placed in a vat 16 and chilled to a temperature less than a critical temperature. Critical temperature is used herein to mean a temperature below which a significant portion of the feedstock is embrittled such that it will break or fracture upon bending, as opposed to flexing, and retains the volatile organic compounds. The temperature of the feedstock may be reduced by exposing it to cryogenic coolants such as chilled gases or liquids. Preferably, the feedstock is chilled by immersion in liquid nitrogen at atmospheric pressures, which is maintained at about 77 K (−196° C.). Other gases and liquids such as a liquid or chilled gaseous carbon dioxide, or similar compounds may be used. It is important that the gas or liquid selected does not chemically react with the feedstock and maintains the temperature low enough to retain organic compounds. The heterogeneous material 12 is reduced to a second smaller sized material 18 by size reduction equipment. The sized material 18 is blended to generate a homogenized mixture 20, which is then sampled to produce a representative sample 22 for analysis. The sized material 18, homogenized material 20, and representative samples are maintained below the critical temperature.

Figure 2:
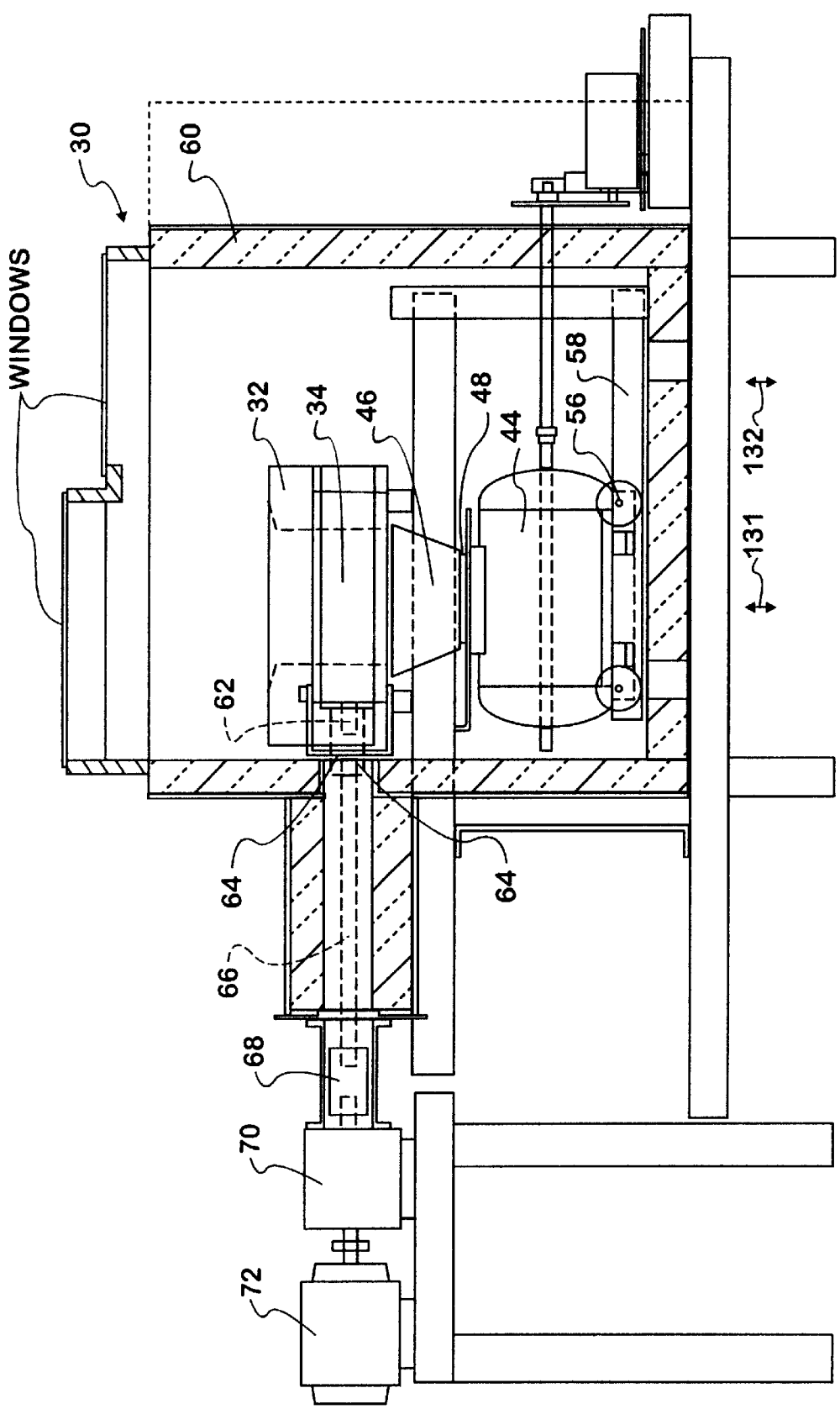
FIG. 2 is a front-plan view of the device of this invention.
Figure 3:
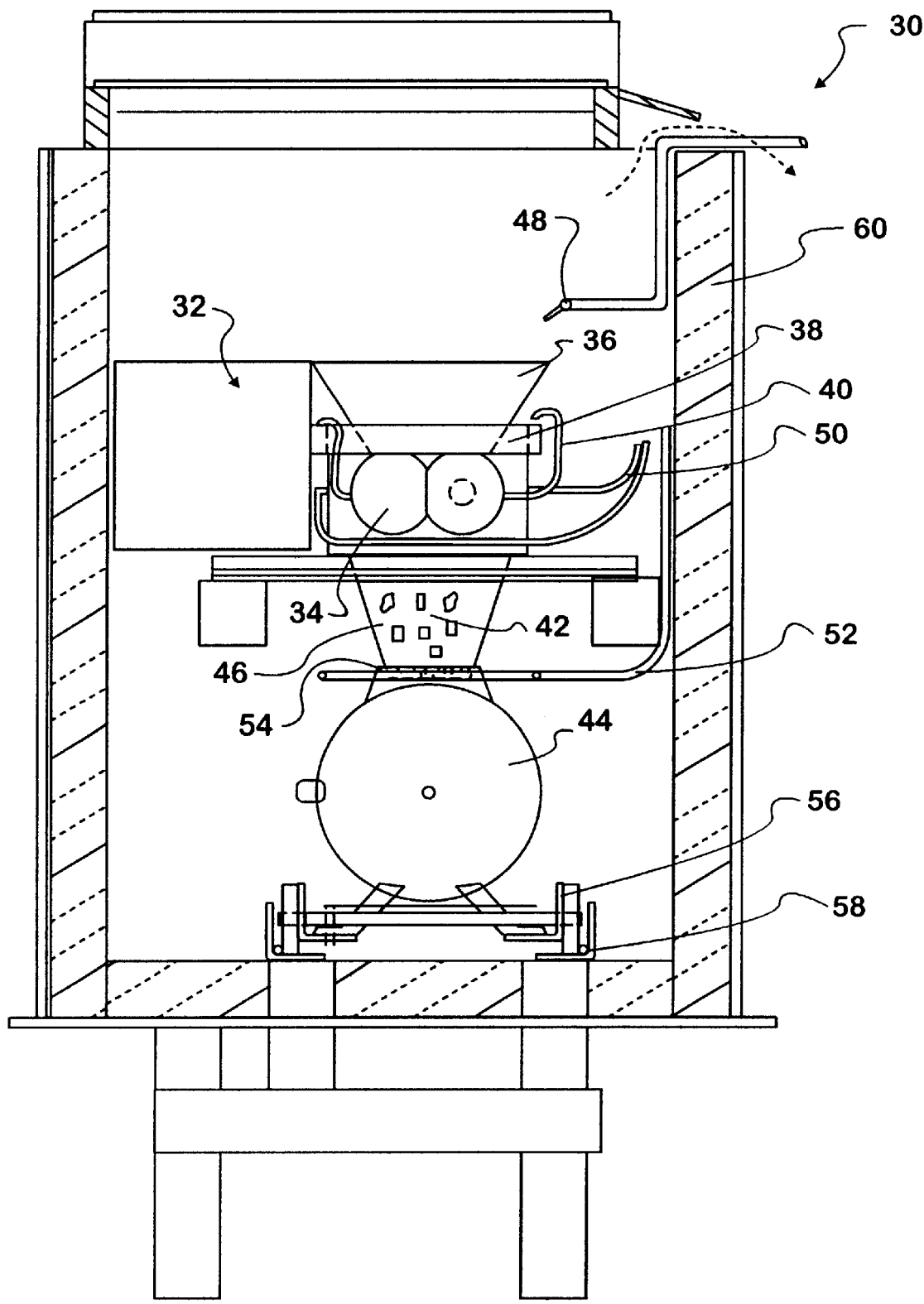
FIG. 3 is a side-plan view of the device of this invention.

The soft waste and size reduction apparatus for use with this invention is shown in FIG. 2 and FIG. 3. generally at 30. Material to be sampled (not shown) is pre chilled to the critical temperature in the precooling vessel 32 in a cryogenic coolant, preferably liquid nitrogen, prior to processing by this device. Material is delivered into the shredder 34 via feed hopper 36 which is cooled by the periodic delivery of a cryogenic coolant to reservoir 38 provided through conduit 40 from the liquid nitrogen storage tank (Not shown). Reduced material 42 from the shredder 34 is transferred to the mixer 44 via hopper 46. The feed hopper 36, shredder 34, and mixer 44 may be cooled, as needed, by a feed of cryogenic coolant via conduits 48, 40 (noted hereinabove), 50, and 52 respectively. Only the equipment is cooled. The pre chilling of the feedstock minimizes the need to spray cryogenic fluid onto feedstack during operation of the process. The blend material is sampled from the mixer 44 by access obtained through mixer opening 54 after the mixer 44 is moved from its normally operating position below the shredder 34 to a second position, by means of roller 56 and track system 58 where access to the mixer 44 can be provided.

The soft waste and size reduction apparatus 30 (as shown in FIGS. 2 and 3) is maintained at a temperature below ambient temperature and preferably at a temperature below the critical temperature. Preferably the critical temperature is liquid nitrogen temperatures 77 K (−196° C.). A cryogenic chamber/cold box 60 as shown in FIGS. 2, 3 surrounds the soft waste and size reduction apparatus 30. Further, each process component of the apparatus 30 is isolated from the ambient environment and the motors used to drive the equipment so that the cold box 60 is maintained at or below ambient temperature. The shredder shaft 62 is coupled via a flexible coupling 64, such as a hex joint, to a low thermal conductivity shaft 66. The low-conductivity shaft 66 is typically constructed from a hollow tube to further reduce the thermal conductivity. The second end of the shredder low-conductivity shredder shaft 66 is coupled by means of a second flexible coupling 68 (U-joint, FIG. 4) to a gear reduction box 70 and motor 72. A counter torque tube 74 connects the gearbox front plate 76 to the shredder support frame 78 to oppose the torque conducted through the shredder shaft 66.

Figure 4:
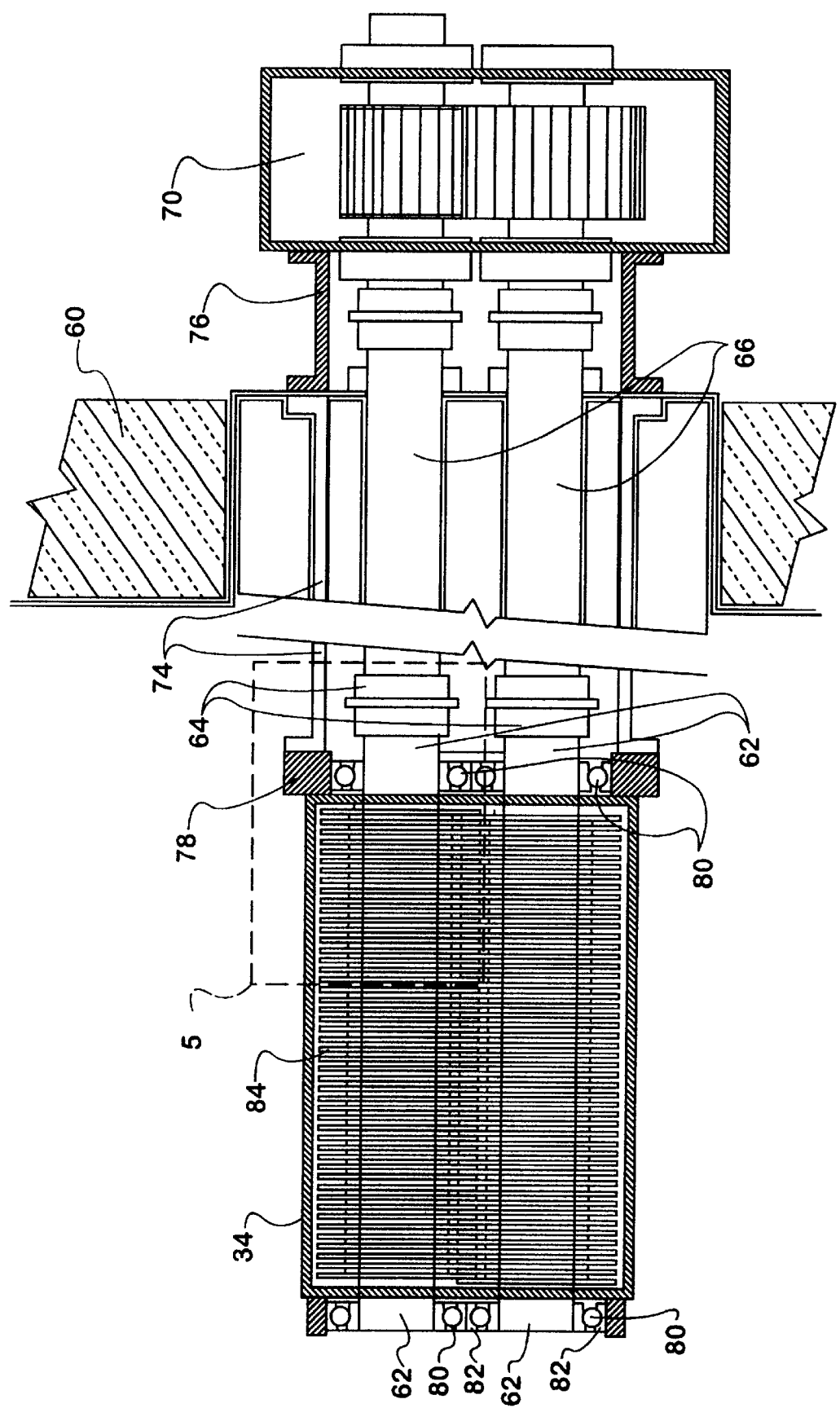
FIG. 4 is a top-plan view of the shredder of this invention.
Figure 5:
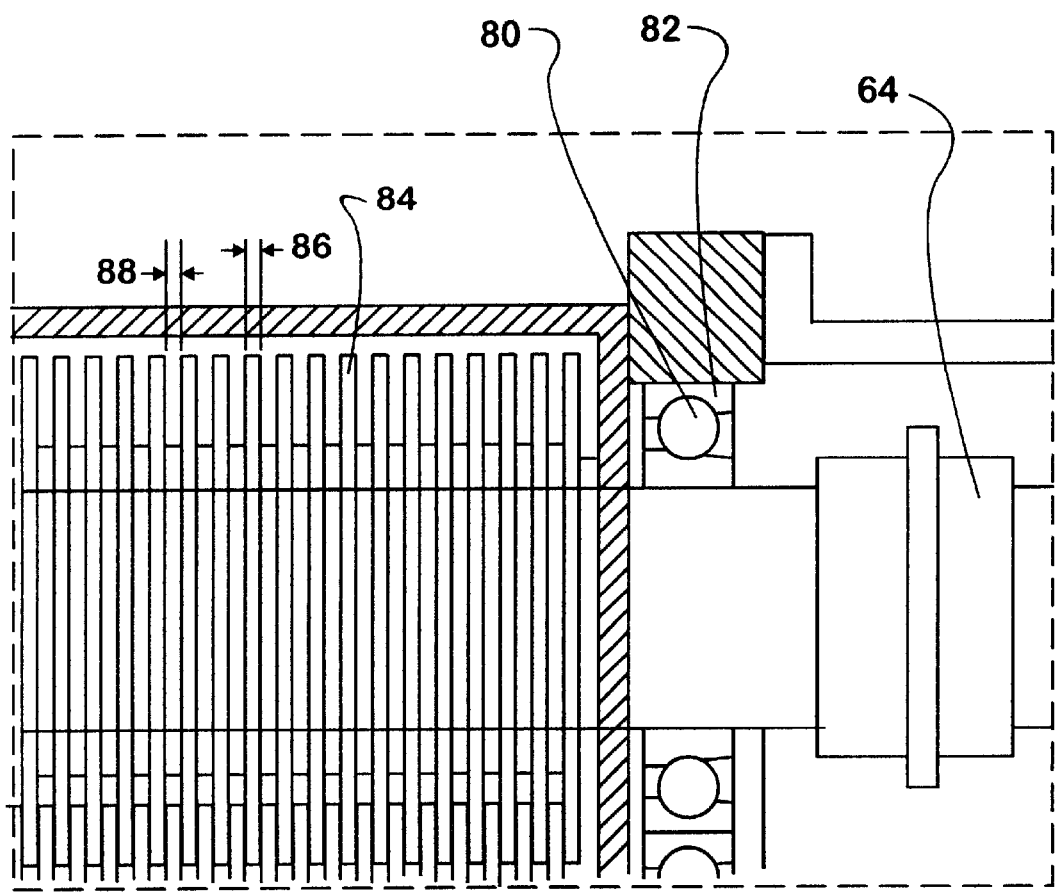
FIG. 5 is an enlarged view of region 5 of FIG. 4.
Figure 6:
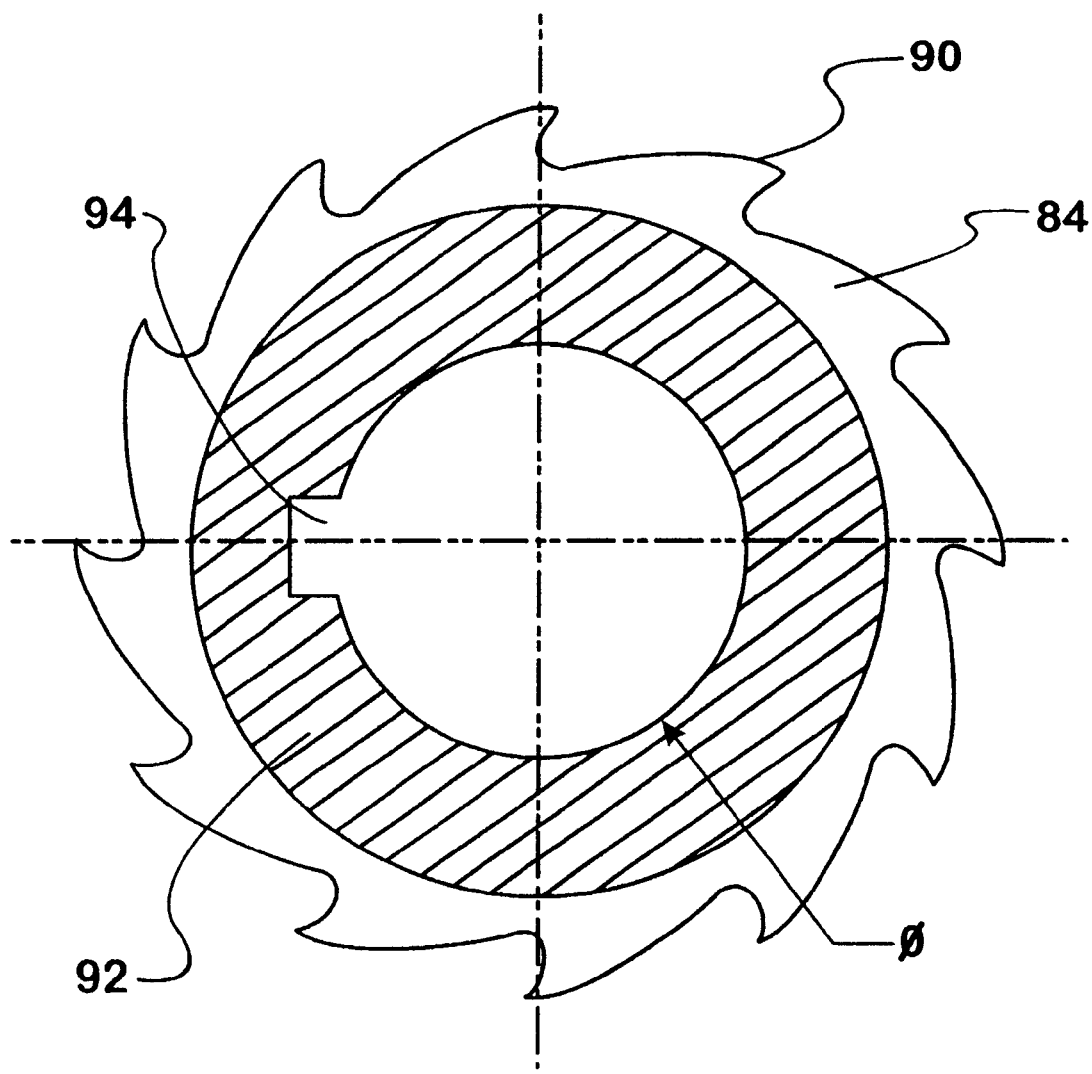
FIG. 6 is a detailed view of one shredder blade.

The shredder 34, the rollers, and the associated drive assembly are shown in a top view in FIG. 4. The shredder 34 for use in the fine or final shredding of the feedstock has been designed for operation at below ambient temperature and in particular, operation at cryogenic temperatures, which preferably is at about liquid nitrogen temperatures. The shredder 34 as shown is constructed of two counter rotating shredder shafts 62 held by bearings 80 held in bearing assemblies 82. The detail construction of the bearing assemblies 82 and cooling system will be discussed later. The cutter blades 84 as shown in FIGS. 4 and 5 are constructed of Maraging 200 steel, or similar material to retain the requisite hardness, yet withstand operation at cryogenic temperatures. The material from which the cutter blades are made must be sufficiently hard to cut brittle polymers and other solids while remaining sufficiently ductile, at temperatures as low as 77 K (−196° C.), to avoid excessive wear or possible shattering. The configuration of the cutter blades 84 for use in the final size reduction of the feedstock is typically such that the thickness 86 and spacing 88 requires the use of narrow gauge materials. Due to the mechanical stresses placed on the cutter blades 84 it is impractical from an operation standpoint to rely on the narrow thickness 86 (Typically on the order of 3 mm) of the cutter blades 84 to conduct the torque from the shredder shaft 62 to the edge 90 of the cutter blade 84, as shown in FIG. 6. Therefore, the cutter blades 84 are constructed in units of 8 or 10 blades that are attached to a central collar 92, (FIG. 6). The collar 92 is keyed 94 to engage with the shredder shaft 62 to provide for the effective transfer of torque from the shredder shaft 62 to the cutter blades 84.

Bearing Assembly

Figure 7:
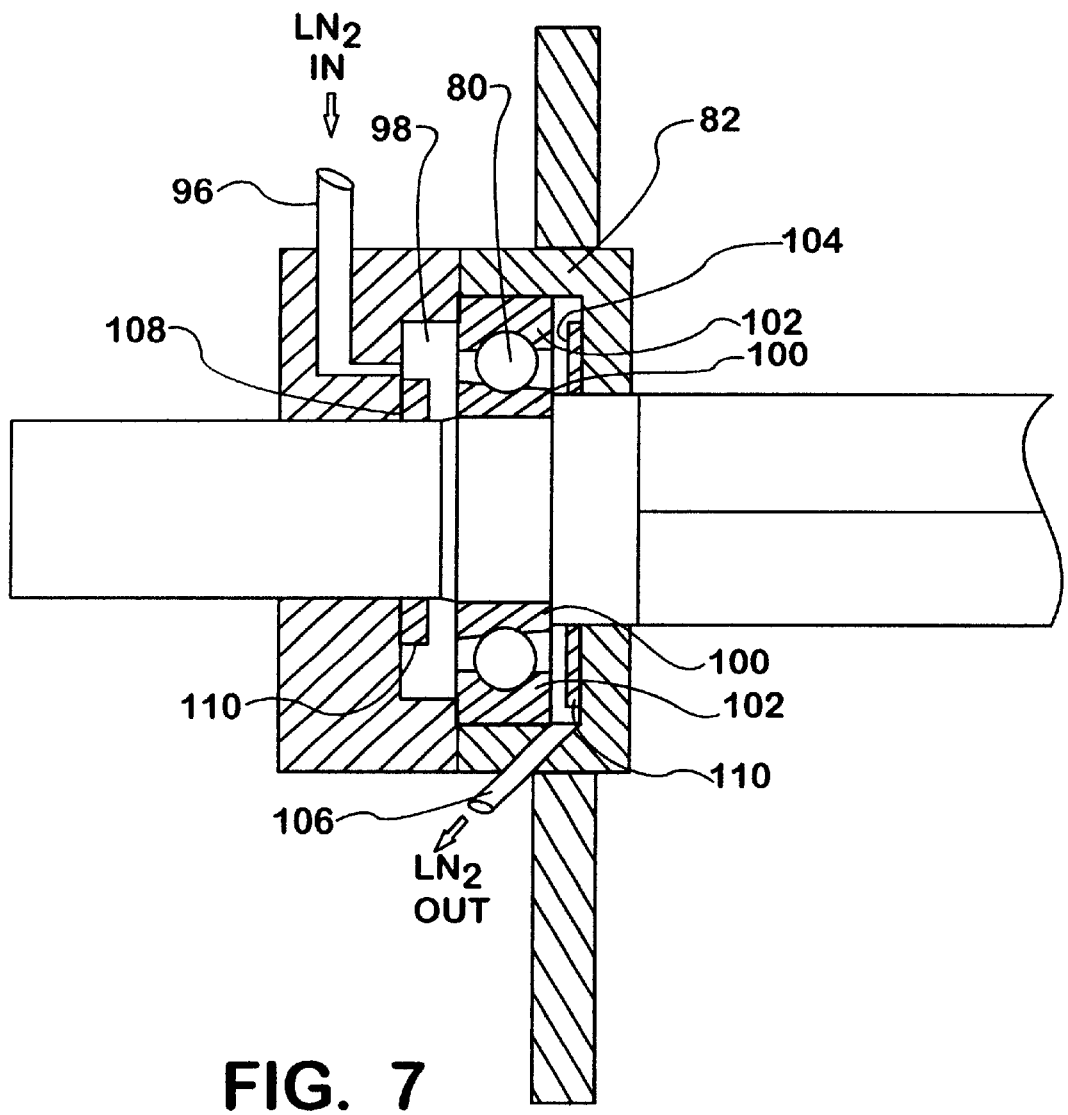
FIG. 7 is a partial cross-sectional view of the shredder bearings for use with this invention.

To remove heat generated by friction within the bearing assembly 82 and to maintain the bearings 80 at the critical temperature a cryogenic cooling system is proposed and is illustrated in FIG. 7. A cryogenic coolant, preferably liquid nitrogen, is fed through inlet conduit 96 to bearing chamber 98. The cryogenic coolant passes around bearings 80 held between inner bearing raceway 100 and outer bearing raceway 102 into reservoir 104. The cryogenic coolant exits the bearing assembly 82 through exhaust conduit 106 and is returned to a cryogenic coolant feed tank (not shown). A drive shaft seal 108 and a cutter shaft seal 110 seal the bearing assembly 82 to prevent the loss of the cryogenic coolant. For the bearings 80 to operate properly at cryogenic temperatures, the bearings must be chilled to cryogenic temperatures then warmed gradually to ambient temperatures before final finishing in order to avoid seizing during operation at cryogenic temperatures, due to a Martensitic transformation.

Mixer Assembly

Figure 8:
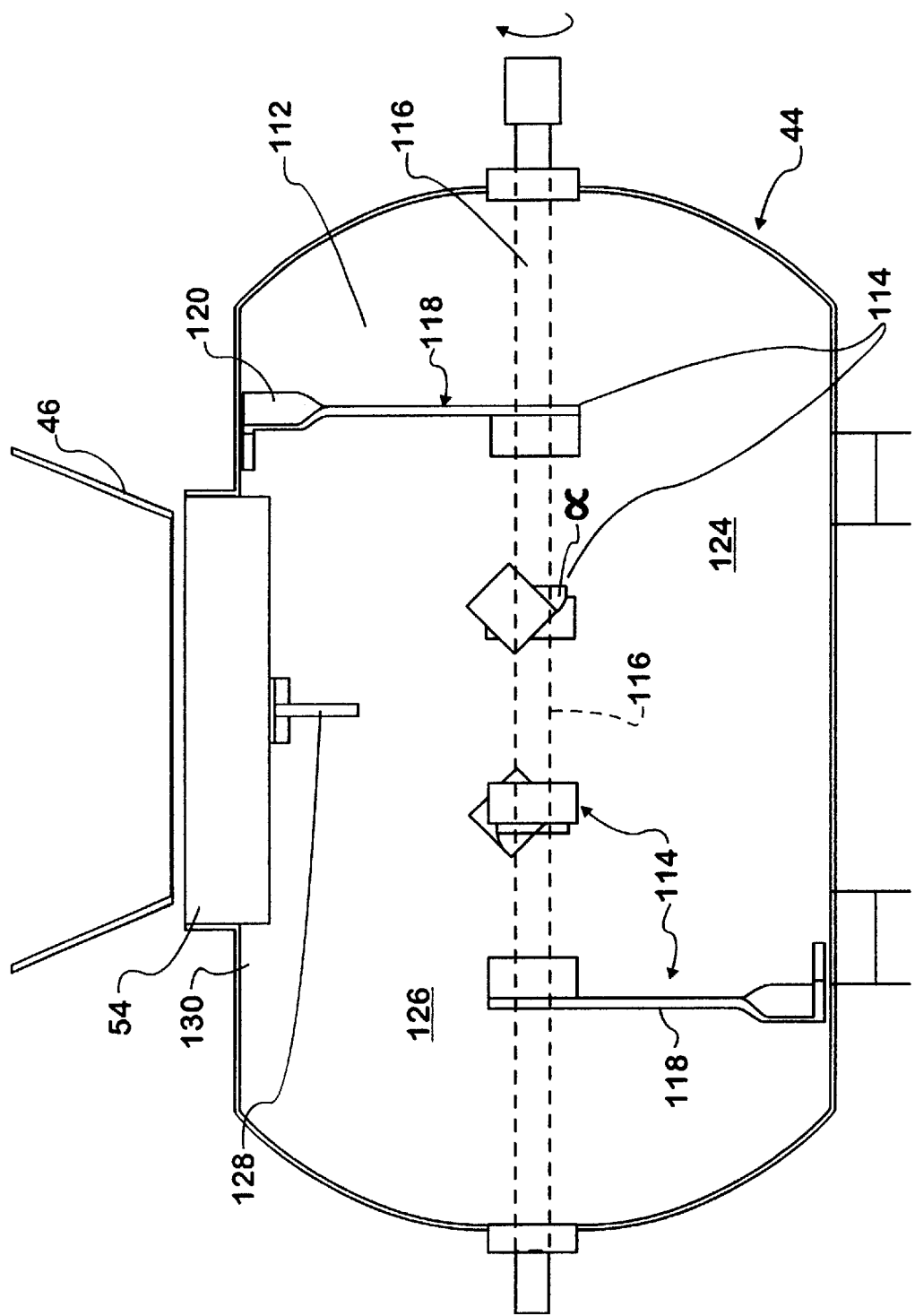
FIG. 8 is a partial cut away front-plan view of the mixing device of this invention.
Figure 9:
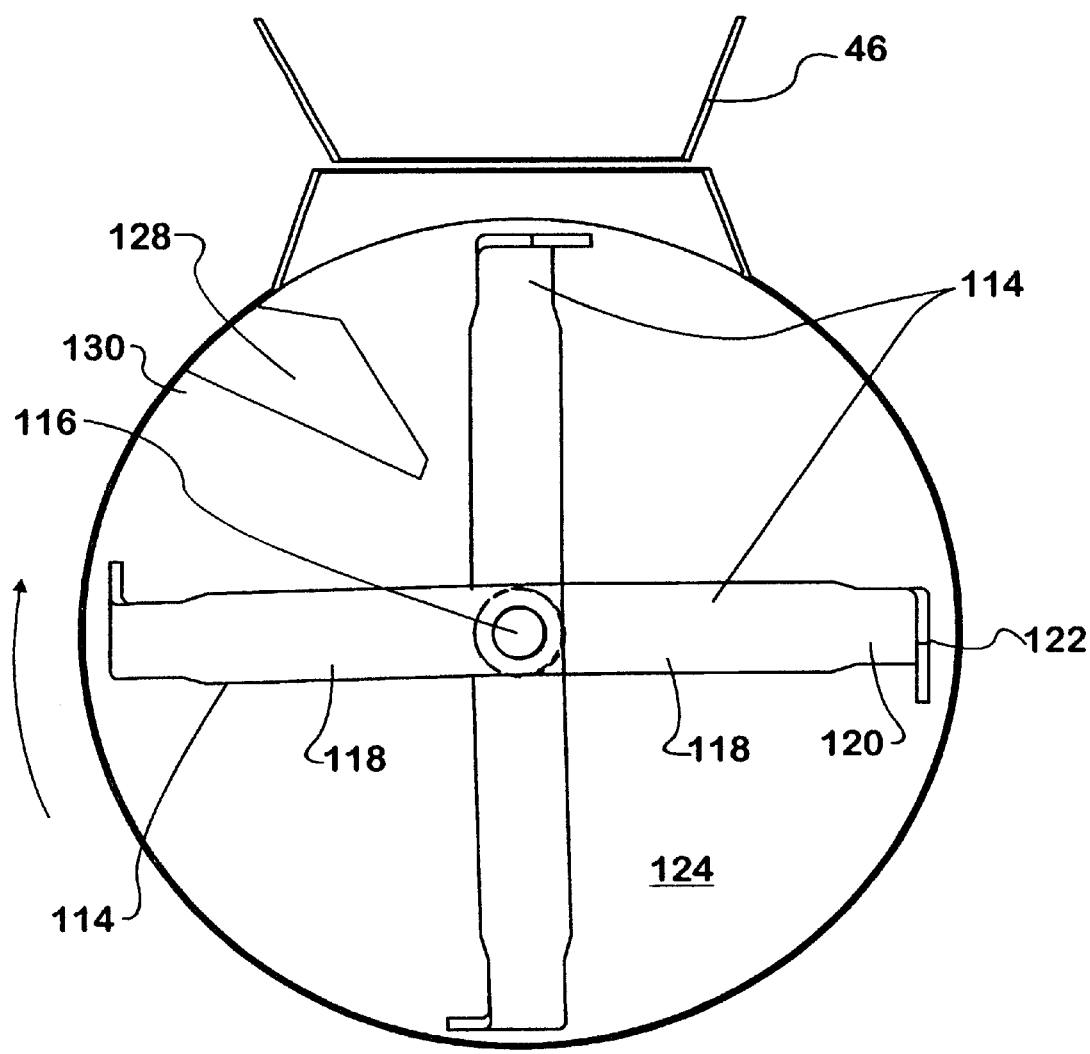
FIG. 9 is a partial cut away side-view illustrating the mixing paddles and blade assembly for use with this invention.

The reduced material 42 exiting the shredder 34 passes through hopper 46 into the mixer 44, which is shown in detail in FIGS. 8 and 9. Reduced material 42 passes through mixer opening 54 of mixer 44 and enters the mixing chamber 112 where it is agitated by mixing paddles 114 affixed to mixer shaft 116. The mixing paddles 114 comprises a paddle arm 118 that is substantially perpendicular to the mixing shaft 116, a rotated paddle section 120 at an angle α from the paddle arm 118, and a paddle base 122 substantially perpendicular to the rotated paddle section 120. The angle α is from about 30° to about 60° and preferably 45°. The mixing paddles 114 are oriented in such a manner that the reduced material 42 is swept toward the center of the mixing chamber 112. For example, for the mixer 44 shown in FIGS. 8 and 9, the rotated paddle sections 120 located in the first section 124 of the mixer 44 are rotated clockwise relative to the paddle arms 118, while the rotated paddle sections 120 located in the second section 126 of the mixer 44 are rotated counter clockwise relative to the paddle arms 118. The reduced material 42 moves to the center of the mixing chamber 112 where it strikes the fixed blade 128 that is affixed to the mixer inner wall 130 adjacent to the mixer opening 54 near the top of the mixer 44. The action of the reduced material 42 impacting on the fixed blade 128 breaks up agglomerations of the reduced material 42, thereby improving the mixing efficiency by providing both axial and radial blending.

Sampling

Figure 10:
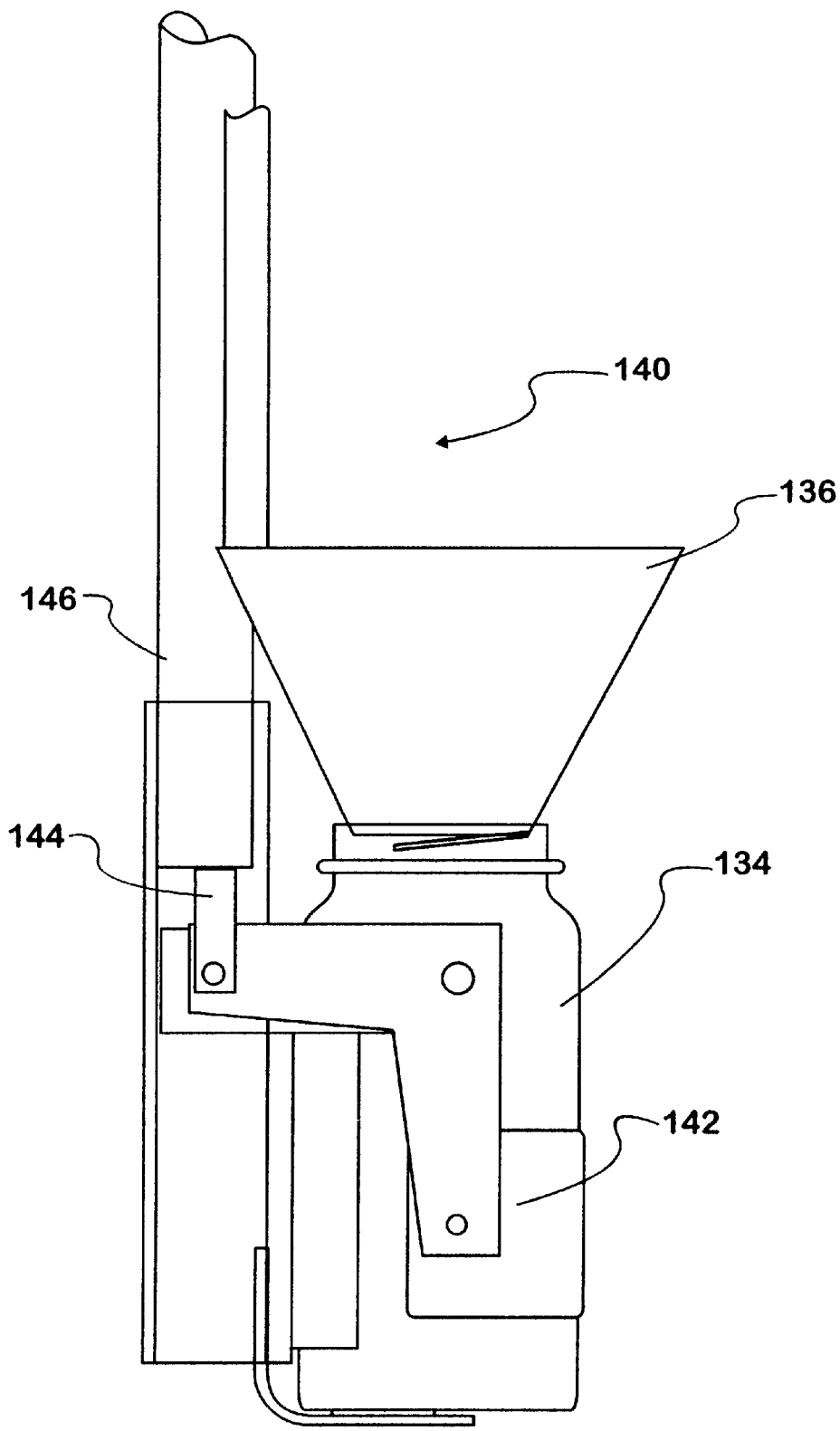
FIG. 10 is a side-plan view of the sampling device for use with this invention.

Representative samples of the reduced material are removed from the mixer 44. The mixer 44 is moved from its operating position 130, as shown in FIG. 2, to the sampling position 132. A representative sample is withdrawn from the mixer 44 with tongs or a clamping device (not shown) and placed in sample bottle 134 as shown in FIG. 10. A funnel 136 directs the reduced material 42 into the sample bottle 134. A manipulator 140 permits handling of the reduced material 42 sample and sample bottle 134 while maintaining the two at cryogenic temperatures. The sample bottle 134 can be clamped into the manipulator 140 with clamp 142 by moving transfer rod 144 within guide tube 146. The sample bottle 134 can then be placed into an insulated storage container (not shown) where it can be maintained at the desired temperature until analyzed. Preferably the sample bottle 134 is maintained at at least the temperature of dry ice (solid $CO_2$) or at liquid nitrogen temperature 77 K (−196° C.).

Preferred Embodiment

Figure 11:
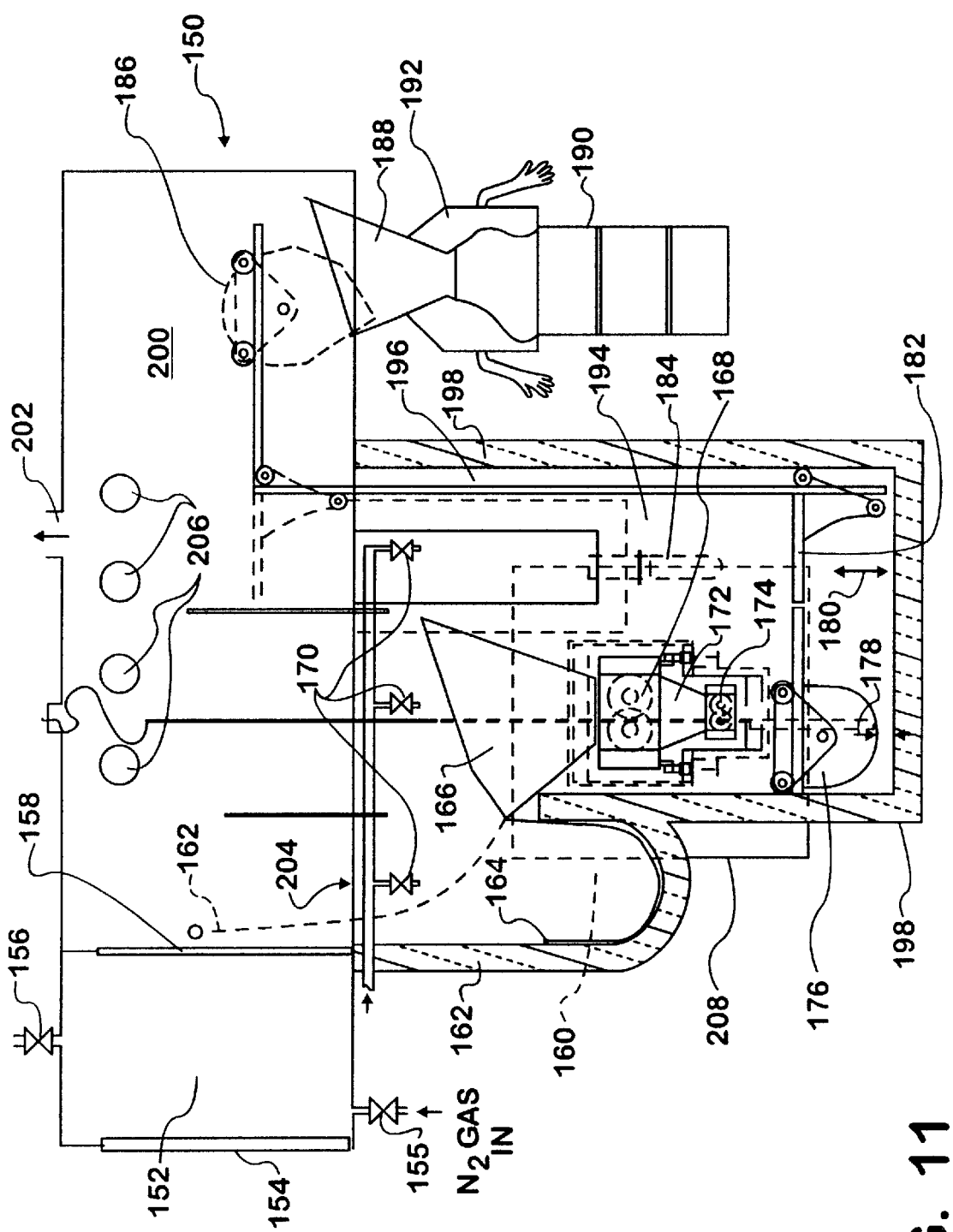
FIG. 11 is a front-plan view of the preferred embodiment of this invention.

In the preferred embodiment, as shown in FIG. 11, feedstock is introduced into the Soft Waste Processing System 150, through air lock 152. The feedstock introduced into the soft waste processing system 150 would normally be the entire contents of one storage vessel (not shown), for example a 55 gallon storage drum. Access to the air lock 152 is obtained through exterior door 154. The air lock 152 is purged with an inert gas, such as nitrogen, argon, or helium, preferably nitrogen, through gas purge inlet 155. The exhaust gas exits through exhaust port 156 and enters a filter system prior to release to the atmosphere. The feedstock introduced into the soft waste process system 150 via air lock 152 passes through interior door 158 where it falls into the pre-chilling vessel 160 that contains the cryogenic fluid, preferably liquid nitrogen. After the feedstock is cooled to below the critical temperature, the feedstock is raised to the discharge position 162 with the aid of moveable screen 164. The material from which the moveable screen 164 is fabricated can be any suitable material that remains flexible and stable at the critical temperature, such as, but not limited to stainless steel or copper. The feedstock falls into the primary shredder feed hopper 166, where it is held prior to introduction into primary shredder 168. The primary shredder 168 reduces the feedstock size from the initial variable size (e.g., 6×2 to 2 in×1 in) to about ½ in×4 in. of the initial average feed size. The feedstock in the primary shredder 168 is maintained at or below the critical temperature by periodic cooling with cryogenic fluid, as needed, through nozzles 170. The primary shredder discharge falls into secondary shredder hopper 172 from which it is fed into the secondary shredder 174, such as a twin-shaft, low speed, high torque shredder. The secondary shredder 174 is similar in design and features to shredder 34 discussed hereinabove. The discharge from the secondary shredder is reduced from about a 4:1 to about 32:1 (final size is on the order of an ⅛ inch square) of the particle size of the feed material fed into the secondary shredder 174.

The feedstock discharged from the secondary shredder 174 enters the mixer 176. After all the feedstock from one vessel has passed through the primary shredder 168 and the secondary shredder 174 and into the mixer 176 the contents would be allowed to mix for a sufficient period of time to permit the contents to stabilize as a homogenous mix. The mixer 176 is then moved from the processing position 178 (indicated by arrows) to the sampling position 180 by means of rail system 182. A representative sample is taken from mixer 176 with sample vessel 184. The representative samples are moved to an insulated storage container (not shown) for retention until analysis of the samples. The samples are preferably maintained at 100 K (−173° C.) or more preferably 77 K (−196° C.) until analyzed. After sampling the mixer 176 is moved to discharge position 186 where it is delivered into discharge hopper 188 and fed into storage vessel 190. The storage vessel 190 may be covered with a glove box system 192 to permit safe handling of the processed secondary waste. The pre-chilling vessel 160, primary shredder 168, secondary shredder 174, mixer 176 and sampling zone 194 are collectively defined as the sample processing zone 196.

The sample processing zone 196 is contained within an insulated chamber 198 in order to maintain the process and equipment at or below the critical temperature. The transport zone 200 located above the sample processing zone 196 may be maintained at a temperature above the critical temperature. Preferably the transport zone 200 is maintained at about ambient temperature and at a slight negative pressure to limit the release of gasses or toxic material from the process. Exhaust is provided through port 202 through a HEPA filter system (not shown) and other gas processing systems. The interface 204 at the top of the sample processing zone 196 is open to the transport zone 200. Additional access to the sample processing zone 196 and the transport zone 200 is provided by glove ports 206 and 208 respectively.

The primary shredder 168 can be a shredder similar to shredder 34, such as a twin-shaft, low speed, high torque shredder or similar shredder. The primary shredder 168 should be constructed from stainless steel or similar material having stability at cryogenic temperatures, in addition to facilitating easy for clean-up and decontamination. The secondary shredder 174 described hereinabove is similar in construction and features to shredder 34 discussed previously. Preferably, the secondary shredder 174 and mixer 176 are constructed from stainless steel or similar material except where noted. The design of mixer 176 is similar to mixer 44 discussed hereinabove.

Thus, in accordance with the invention, there has been provided a process that will retain volatile organic compounds contained within a feedstock during the sampling procedure. There has also been provided a representative sample from heterogenous feedstock. There has also been provided a process that is consistent with the hazardous waste regulations. There has also been provided a process that reduces the number of samples required to adequately characterize a population of heterogeneous waste. Additionally, there has been provided a contained apparatus such that the apparatus is maintained at cryogenic operating conditions and minimizes the spread of radioactive and/or hazardous material and personnel exposure.

With this description of the invention in detail, those skilled in the art will appreciate that modification may be made to the invention without departing form the spirit thereof. Therefore, it is not intended that the scope of the invention be limited to the specific embodiments that have been illustrated and described. Rather, it is intended that the scope to the invention be determined by the scope of the appended claims.

We claim:

1. A process/method for providing a representative analytical sample comprising:

providing a heterogenous feedstock, including volatile organic compounds, having an average initial particle/object/component size;

reducing the temperature of the heterogeneous feedstock to a temperature below a critical temperature;

conveying the heterogeneous feedstock to a size reduction device;

reducing the size of the feedstock components, wherein the size reduction step takes place below the critical temperature;

blending the reduced size feedstock to form a homogeneous mixture, wherein the blending step takes place below the critical temperature;

obtaining a representative sample of the homogeneous mixture.

2. The process of claim 1 further comprising maintaining the representative sample below the critical temperature until analyzed.

3. The process of claim 2 further comprising maintaining the representative sample below 77 K (−196° C.) until analyzed.

4. The process of claim 1 wherein the critical temperature is less than about 100 K (−173° C.).

5. The process of claim 1 wherein the critical temperature is less than about 77 K (−196° C.).

6. The process of claim 1 wherein the reduction of size of the sample and the blending step take place simultaneously.

7. The process of claim 1 where volatile organic compounds present in the feedstock are retained in the representative sample.

8. The process of claim 1 wherein liquid nitrogen is used to reduce the temperature of the feedstock below the critical temperature.

9. An apparatus for providing a homogeneous analytical sample from a heterogeneous feedstock, including volatile organic compounds, comprising:

a means for reducing the temperature of the heterogeneous feedstock, including volatile organic compounds, to a temperature below a critical temperature;

a size reduction device in fluid communication with the temperature reduction means, wherein size reduction device is maintained at a temperature less than the critical temperature;

a blending device in fluid communication with the size reduction device wherein the reduced size feedstock is blended to form a homogeneous mixture and wherein the blending device is maintained at a temperature less than the critical temperature; and a transport means for removing a representative sample from the blending device;

a sampling device in fluid communication with the transport means for accepting a representative sample of the homogeneous mixture.

10. The apparatus of claim 9 further comprising a means for maintaining the representative sample below the critical temperature until analyzed.

11. The apparatus of claim 9 further comprising maintaining the representative sample below 77 K (−196° C.) until analyzed.

12. The apparatus of claim 9 wherein the size reduction device and the blending device are a single device.

13. The apparatus of claim 9 where volatile organic compounds present in the feedstock are retained in the representative sample.

14. The apparatus of claim 9 wherein the critical temperature is maintained with liquid nitrogen.

* * * * *